United States Patent
Van Der Linde

(10) Patent No.: US 10,697,003 B2
(45) Date of Patent: Jun. 30, 2020

(54) MARKER FOR COMPACT GROWTH IN CUCUMBER

(71) Applicant: RIJK ZWAAN ZAADTEELT EN ZAADHANDEL B.V., De Lier (NL)

(72) Inventor: Lilian Van Der Linde, De Lier (NL)

(73) Assignee: RIJK ZWAAN ZAADTEELT EN ZAADHANDEL B.V., De Lier (NL)

(*) Notice: Subject to any disclaimer, the term of this patent is extended or adjusted under 35 U.S.C. 154(b) by 0 days.

(21) Appl. No.: 15/893,901

(22) Filed: Feb. 12, 2018

(65) Prior Publication Data

US 2018/0187244 A1 Jul. 5, 2018

Related U.S. Application Data

(63) Continuation-in-part of application No. PCT/EP2016/071179, filed on Sep. 8, 2016.

(30) Foreign Application Priority Data

Sep. 8, 2015 (NL) .................................... 2015408

(51) Int. Cl.
| | | |
|---|---|---|
| A01H 1/04 | (2006.01) | |
| C12Q 1/68 | (2018.01) | |
| C12Q 1/6809 | (2018.01) | |
| A01H 5/08 | (2018.01) | |
| C12Q 1/6895 | (2018.01) | |
| C12Q 1/6858 | (2018.01) | |
| A01H 1/02 | (2006.01) | |

(52) U.S. Cl.
CPC .............. *C12Q 1/6809* (2013.01); *A01H 1/04* (2013.01); *A01H 5/08* (2013.01); *C12Q 1/6858* (2013.01); *C12Q 1/6895* (2013.01); *A01H 1/02* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2011/0047642 A1   2/2011   Crienen et al.

FOREIGN PATENT DOCUMENTS

| WO | 2009/059777 | 5/2009 | |
| WO | WO-2009059777 A1 * | 5/2009 | ............... A01H 5/00 |

OTHER PUBLICATIONS

Rubinstein et al 2015 PLOSone 1-19, provided by Applicant (Year: 2015).*
International Search Report and Written Opinion of the International Searching Authority dated Dec. 7, 2016 which issued during prosecution of International Application No. PCT/EP2016/071179.
Li, et al. "Fine genetic mapping of cp: a recessive gene for compact (dwarf) plant architecture in cucumber, *Cucumis sativus* L." Theoretical and Applied Genetics, Jul. 2011, 123(6):973-983.
Rubenstein, et al. "Ultrahigh-Density Linkage Map for Cultivated Cucumber (*Cucumis sativus* L.) Using a Single-Nucleotide Polymorphism Genotyping Array" PLOS ONE, Apr. 2015, 10(4):e0124101.
Xin, et al. "Genetic identification of a dwarf mutant in cucumber (*Cucumis sativus* L.)" African Journal of Biotechnology, Mar. 2012, 11(20):4493-4498.

* cited by examiner

*Primary Examiner* — Brent T Page
(74) *Attorney, Agent, or Firm* — Duane Morris LLP; Thomas J. Kowalski; Deborah L. Lu

(57) ABSTRACT

The present invention relates to a marker for identifying a cucumber plant showing a compact growth phenotype, characterized by a shorter internode length and/or a smaller leaf area. The marker comprises a mutation in the Cullin1 gene, thereby providing cucumber plants with a shorter internode length and/or a smaller leaf area when compared to cucumber plants without the mutation in the Cullin1 gene. A plant that shows the resulting compact growth phenotype is in particular suitable for high-wire cultivation. Furthermore, the invention also relates to the use of a modified cucumber Cullin1 gene or a part thereof for identifying a cucumber plant showing a shorter internode length and/or a smaller leaf area.

6 Claims, 2 Drawing Sheets

Specification includes a Sequence Listing.

Fig. 1

ATGACAATGGGCGAGCGGAAGACTATTGACTTGGAGCAGGGATGGGAGTTTATGCAGAAGGGTATCACAAAGT
TGAAGAACATTCTCGAGGGCTTGCCTGAGCCTCAGTTCAGCTCCGAGGACTACATGATGCTTTACACTACCAT
[A]TATAACATGTGCACCCAAAAGCCGCCGCATGATTACTCCCAGCAGCTGTATGATAAATATCGTGAATCTT
TTGAAGAGTACATCACTTCTATGGTCTTACCATCCTTGAGGGAGAAGCACGATGAGTTCATGTTGAGAGAACT
AGTAAAAAGGTGGACAAACCATAAAGTCATGGTGAGGTGGCTTTCTCGCTTCTTCCACTATCTTGATCGGTAC
TTCATCGCTCGAAGGTCACTTCCACCTCTAAATGAAGTTGGCCTCACATGCTTCCGCGAATTGGTGTACAAAG
AGCTAAATAGTAAAGTGAGGGATGCAGTAATTTCATTGATTGATCAAGAACGTGAAGGAGAACAGATTGACAG
AGCTCTACTGAAGAATGTACTAGATATATTTGTGGAAATTGGTATGGGCAAATGGATTACTATGAAAATGAC
TTTGAAGCTGCCATGCTTAAAGATACTGCTGCTTATTACTCTAGGAAGGCTTCCAATTGGATCCTAGAAGATT
CTTGTCCCGATTATATGCTTAAAGCAGAGGAGTGCTTGAAACGAGAAAAGGATAGGGTTTCCCACTATTTGCA
CTCTAGTAGCGAGCCAAAGTTGTTGGAGAAAGTTCAACATGAACTATTATCTGTTTATGCTACTCAACTGCTG
GAAAAAGAGCATTCAGGATGCCATGCATTGCTTAGAGATGACAAGGTGGAAGATTTGTCAAGGATGTTCCGTC
TATTCTCCAAAATACCGAAGGGACTGGATCCAGTTTCCAACATATTTAAGCAGCATGTAACTGCTGAAGGAAC
AGCACTGGTCAAACAGGCAGAAGATGCTGCAAGTAACAAGAAGGCTGAGAAAAAGGACATAGTTGGTCTGCAG
GAACAGGTTTTTGTAAGAAAAGTGATTGAGCTTCACGACAAGTACTTGGCTTATGTGAATGATTGTTTCCAAA
ACCACACACTTTTCCATAAGGCTCTCAAGGAAGCTTTTGAAGTATTTTGCAATAAGGGTGTTGCTGGAAGTTC
TAGTGCAGAATTGCTTGCTACCTTTTGTGATAACATCCTTAAGAAAGGTGGGAGTGAGAAGTTGAGTGATGAA
GCAATCGAGGAGACACTTGAGAAGGTTGTGAAGTTGTTGGCATACATTTGCGACAAAGATCTGTTTGCTGAAT
TCTATAGAAAAAAACTTGCCCGAAGGCTTCTCTTTGACAAGAGCGCGAACGATGACCACGAGAGAAGTATATT
GACCAAATTGAAGCAACAATGTGGTGGTCAGTTCACTTCTAAGATGGAGGGAATGGTTACTGATTTGACTTTG
GCAAGGGAGAACCAAACTAGTTTTGAGGAGTATCTGAGCAATAATCCACAAGCGAGTCCTGGCATCGACCTGA
CTGTTACTGTTTTAACTACTGGATTTTGGCCAAGCTACAAGTCTTTTGACCTCAACCTGCCGGCAGAGATGGT
AAAGTGTGTTGAAGTTTTCAGAGAGTTTTATCAAACAAAAACCAAGCATCGAAAACTTACATGGATTTACTCA
TTGGGTACTTGTAACATCAGTGGAAAATTTGAACCGAAAACGATGGAGCTGATTGTGACAACTTATCAGGCTT
CTGCCCTGTTGCTATTCAATTCTTCGGATAGACTAAGTTACTCGGAAATCATGACACAATTAAATTTGAGTGA
CGATGATGTAGTTAGACTACTCCACTCGTTGTCATGTGCCAAGTATAAAATTCTTAATAAGGAACCAAATACG
AAAACCATCTCTCCGAACGATCATTTTGAGTTCAATGCAAAATTCTCCGACAAAATGAGGAGAATAAAGATCC
CTCTTCCGCCTGTGGATGAGAAAAAGAAAGTCATTGAAGATGTTGACAAGGATCGAAGGTATGCTATTGACGC
CTCAATCGTGCGTATCATGAAGAGTCGGAAAGTTCTTGGTCATCAGCAACTAGTGATGGAGTGCGTCGAGCAA
TTGGGCCGTATGTTCAAGCCCGATTTCAAGGCGATAAAGAAGAGAATTGAAGACCTGATCACTCGGGATTATC
TAGAGAGAGACAAAGACAACCCCCACTTGTTTAGGTACTTGGCTTGA

Fig. 2

ATGACAATGGGCGAGCGGAAGACTATTGACTTGGAGCAGGGATGGGAGTTTATGCAGAAGGGTATCACAAAGT
TGAAGAACATTCTCGAGGGCTTGCCTGAGCCTCAGTTCAGCTCCGAGGACTACATGATGCTTTACACTACCAT
[G]TATAACATGTGCACCCAAAAGCCGCCGCATGATTACTCCCAGCAGCTGTATGATAAATATCGTGAATCTT
TTGAAGAGTACATCACTTCTATGGTCTTACCATCCTTGAGGGAGAAGCACGATGAGTTCATGTTGAGAGAACT
AGTAAAAAGGTGGACAAACCATAAAGTCATGGTGAGGTGGCTTTCTCGCTTCTTCCACTATCTTGATCGGTAC
TTCATCGCTCGAAGGTCACTTCCACCTCTAAATGAAGTTGGCCTCACATGCTTCCGCGAATTGGTGTACAAAG
AGCTAAATAGTAAAGTGAGGGATGCAGTAATTTCATTGATTGATCAAGAACGTGAAGGAGAACAGATTGACAG
AGCTCTACTGAAGAATGTACTAGATATATTTGTGGAAATTGGTATGGGCAAATGGATTACTATGAAAATGAC
TTTGAAGCTGCCATGCTTAAAGATACTGCTGCTTATTACTCTAGGAAGGCTTCCAATTGGATCCTAGAAGATT
CTTGTCCCGATTATATGCTTAAAGCAGAGGAGTGCTTGAAACGAGAAAAGGATAGGGTTTCCCACTATTTGCA
CTCTAGTAGCGAGCCAAAGTTGTTGGAGAAAGTTCAACATGAACTATTATCTGTTTATGCTACTCAACTGCTG
GAAAAAGAGCATTCAGGATGCCATGCATTGCTTAGAGATGACAAGGTGGAAGATTTGTCAAGGATGTTCCGTC
TATTCTCCAAAATACCGAAGGGACTGGATCCAGTTTCCAACATATTTAAGCAGCATGTAACTGCTGAAGGAAC
AGCACTGGTCAAACAGGCAGAAGATGCTGCAAGTAACAAGAAGGCTGAGAAAAAGGACATAGTTGGTCTGCAG
GAACAGGTTTTTGTAAGAAAAGTGATTGAGCTTCACGACAAGTACTTGGCTTATGTGAATGATTGTTTCCAAA
ACCACACACTTTTCCATAAGGCTCTCAAGGAAGCTTTTGAAGTATTTTGCAATAAGGGTGTTGCTGGAAGTTC
TAGTGCAGAATTGCTTGCTACCTTTTGTGATAACATCCTTAAGAAAGGTGGGAGTGAGAAGTTGAGTGATGAA
GCAATCGAGGAGACACTTGAGAAGGTTGTGAAGTTGTTGGCATACATTTGCGACAAAGATCTGTTTGCTGAAT
TCTATAGAAAAAAACTTGCCCGAAGGCTTCTCTTTGACAAGAGCGCGAACGATGACCACGAGAGAAGTATATT
GACCAAATTGAAGCAACAATGTGGTGGTCAGTTCACTTCTAAGATGGAGGGAATGGTTACTGATTTGACTTTG
GCAAGGGAGAACCAAACTAGTTTTGAGGAGTATCTGAGCAATAATCCACAAGCGAGTCCTGGCATCGACCTGA
CTGTTACTGTTTTAACTACTGGATTTTGGCCAAGCTACAAGTCTTTTGACCTCAACCTGCCGGCAGAGATGGT
AAAGTGTGTTGAAGTTTTCAGAGAGTTTTATCAAACAAAAACCAAGCATCGAAAACTTACATGGATTTACTCA
TTGGGTACTTGTAACATCAGTGGAAAATTTGAACCGAAAACGATGGAGCTGATTGTGACAACTTATCAGGCTT
CTGCCCTGTTGCTATTCAATTCTTCGGATAGACTAAGTTACTCGGAAATCATGACACAATTAAATTTGAGTGA
CGATGATGTAGTTAGACTACTCCACTCGTTGTCATGTGCCAAGTATAAAATTCTTAATAAGGAACCAAATACG
AAAACCATCTCTCCGAACGATCATTTTGAGTTCAATGCAAAATTCTCCGACAAAATGAGGAGAATAAAGATCC
CTCTTCCGCCTGTGGATGAGAAAAAGAAAGTCATTGAAGATGTTGACAAGGATCGAAGGTATGCTATTGACGC
CTCAATCGTGCGTATCATGAAGAGTCGGAAAGTTCTTGGTCATCAGCAACTAGTGATGGAGTGCGTCGAGCAA
TTGGGCCGTATGTTCAAGCCCGATTTCAAGGCGATAAAGAAGAGAATTGAAGACCTGATCACTCGGGATTATC
TAGAGAGAGACAAAGACAACCCCCACTTGTTTAGGTACTTGGCTTGA

SEQUENCE LISTING

<160> NUMBER OF SEQ ID NOS: 2

<210> SEQ ID NO 1
<211> LENGTH: 2235
<212> TYPE: DNA
<213> ORGANISM: Cucumis sativus
<220> FEATURE:
<221> NAME/KEY: source
<222> LOCATION: 1..2235
<223> OTHER INFORMATION: /organism="Cucumis sativus"
      /mol_type="unassigned DNA"

<400> SEQUENCE: 1

| | | | | | |
|---|---|---|---|---|---|
| atgacaatgg | gcgagcggaa | gactattgac | ttggagcagg | gatgggagtt | tatgcagaag | 60 |
| ggtatcacaa | agttgaagaa | cattctcgag | ggcttgcctg | agcctcagtt | cagctccgag | 120 |
| gactacatga | tgctttacac | taccatatat | aacatgtgca | cccaaaagcc | gccgcatgat | 180 |
| tactcccagc | agctgtatga | taaatatcgt | gaatcttttg | aagagtacat | cacttctatg | 240 |
| gtcttaccat | ccttgaggga | gaagcacgat | gagttcatgt | tgagagaact | agtaaaaagg | 300 |
| tggacaaacc | ataaagtcat | ggtgaggtgg | ctttctcgct | tcttccacta | tcttgatcgg | 360 |
| tacttcatcg | ctcgaaggtc | acttccacct | ctaaatgaag | ttggcctcac | atgcttccgc | 420 |
| gaattggtgt | acaaagagct | aaatagtaaa | gtgagggatg | cagtaatttc | attgattgat | 480 |
| caagaacgtg | aaggagaaca | gattgacaga | gctctactga | agaatgtact | agatatattt | 540 |
| gtggaaattg | gtatgggggca | aatggattac | tatgaaaatg | actttgaagc | tgccatgctt | 600 |
| aaagatactg | ctgcttatta | ctctaggaag | gcttccaatt | ggatcctaga | agattcttgt | 660 |
| cccgattata | tgcttaaagc | agaggagtgc | ttgaaacgag | aaaaggatag | ggtttcccac | 720 |
| tatttgcact | ctagtagcga | gccaaagttg | ttggagaaag | ttcaacatga | actattatct | 780 |
| gtttatgcta | ctcaactgct | ggaaaaagag | cattcaggat | gccatgcatt | gcttagagat | 840 |
| gacaaggtgg | aagatttgtc | aaggatgttc | cgtctattct | ccaaaatacc | gaagggactg | 900 |
| gatccagttt | ccaacatatt | taagcagcat | gtaactgctg | aaggaacagc | actggtcaaa | 960 |
| caggcagaag | atgctgcaag | taacaagaag | gctgagaaaa | aggacatagt | tggtctgcag | 1020 |
| gaacaggttt | ttgtaagaaa | agtgattgag | cttcacgaca | agtacttggc | ttatgtgaat | 1080 |
| gattgtttcc | aaaaccacac | acttttccat | aaggctctca | aggaagcttt | tgaagtattt | 1140 |
| tgcaataagg | gtgttgctgg | aagttctagt | gcagaattgc | ttgctaccct | tgtgataac | 1200 |
| atccttaaga | aaggtgggag | tgagaagttg | agtgatgaag | caatcgagga | gacacttgag | 1260 |
| aaggttgtga | agttgttggc | atacatttgc | gacaaagatc | tgtttgctga | attctataga | 1320 |
| aaaaaacttg | cccgaaggct | tctctttgac | aagagcgcga | acgatgacca | cgagagaagt | 1380 |
| atattgacca | aattgaagca | acaatgtggt | ggtcagttca | cttctaagat | ggagggaatg | 1440 |
| gttactgatt | tgactttggc | aagggagaac | caaactagtt | ttgaggagta | tctgagcaat | 1500 |
| aatccacaag | cgagtcctgg | catcgacctg | actgttactg | ttttaactac | tggattttgg | 1560 |
| ccaagctaca | agtcttttga | cctcaacctg | ccggcagaga | tggtaaagtg | tgttgaagtt | 1620 |
| ttcagagagt | tttatcaaac | aaaaaccaag | catcgaaaac | ttacatggat | ttactcattg | 1680 |
| ggtacttgta | acatcagtgg | aaaatttgaa | ccgaaaacga | tggagctgat | tgtgacaact | 1740 |
| tatcaggctt | ctgccctgtt | gctattcaat | tcttcggata | gactaagtta | ctcggaaatc | 1800 |
| atgacacaat | taaatttgag | tgacgatgat | gtagttagac | tactccactc | gttgtcatgt | 1860 |

```
gccaagtata aaattcttaa taaggaacca aatacgaaaa ccatctctcc gaacgatcat    1920
tttgagttca atgcaaaatt ctccgacaaa atgaggagaa taaagatccc tcttccgcct    1980
gtggatgaga aaagaaagt cattgaagat gttgacaagg atcgaaggta tgctattgac    2040
gcctcaatcg tgcgtatcat gaagagtcgg aaagttcttg gtcatcagca actagtgatg    2100
gagtgcgtcg agcaattggg ccgtatgttc aagcccgatt tcaaggcgat aaagaagaga    2160
attgaagacc tgatcactcg ggattatcta gagagagaca agacaaccc ccacttgttt    2220 aggtacttgg cttga                                                    2235
```

<210> SEQ ID NO 2
<211> LENGTH: 2235
<212> TYPE: DNA
<213> ORGANISM: Cucumis sativus
<220> FEATURE:
<221> NAME/KEY: source
<222> LOCATION: 1..2235
<223> OTHER INFORMATION: /organism="Cucumis sativus"
      /mol_type="unassigned DNA"

<400> SEQUENCE: 2

```
atgacaatgg gcgagcggaa gactattgac ttggagcagg gatgggagtt tatgcagaag      60
ggtatcacaa agttgaagaa cattctcgag ggcttgcctg agcctcagtt cagctccgag     120
gactacatga tgctttacac taccatgtat aacatgtgca cccaaaagcc gccgcatgat     180
tactcccagc agctgtatga taaatatcgt gaatcttttg aagagtacat cacttctatg     240
gtcttaccat ccttgaggga aagcacgat gagttcatgt tgagagaact agtaaaaagg     300
tggacaaacc ataaagtcat ggtgaggtgg cttctctcgct tcttccacta tcttgatcgg     360
tacttcatcc tcgaaggtc acttccacct ctaaatgaag ttggcctcac atgcttccgc     420
gaattggtgt acaaagagct aaatagtaaa gtgagggatg cagtaatttc attgattgat     480
caagaacgtg aaggagaaca gattgacaga gctctactga agaatgtact agatatattt     540
gtggaaattg gtatggggca aatggattac tatgaaaatg actttgaagc tgccatgctt     600
aaagatactg ctgcttatta ctctaggaag gcttccaatt ggatcctaga agattcttgt     660
cccgattata tgcttaaagc agaggagtgc ttgaaacgag aaaaggatag ggtttcccac     720
tatttgcact ctagtagcga gccaaagttg ttggagaaag ttcaacatga actattatct     780
gtttatgcta ctcaactgct ggaaaaagag cattcaggat gccatgcatt gcttagagat     840
gacaaggtgg aagatttgtc aaggatgttc cgtctattct ccaaaatacc gaagggactg     900
gatccagttt ccaacatatt taagcagcat gtaactgctg aaggaacagc actggtcaaa     960
caggcagaag atgctgcaag taacaagaag gctgagaaaa aggacatagt tggtctgcag    1020
gaacaggttt ttgtaagaaa agtgattgag cttcacgaca agtacttggc ttatgtgaat    1080
gattgtttcc aaaaccacac acttttccat aaggctctca aggaagcttt tgaagtattt    1140
tgcaataagg gtgttgctgg aagttctagt gcagaattgc ttgctacctt ttgtgataac    1200
atccttaaga aggtgggag tgagaagttg agtgatgaag caatcgagga gacacttgag    1260
aaggttgtga agtgttggc atacatttgc gacaaagatc tgtttgctga attctataga    1320
aaaaaacttg cccgaaggct tctctttgac aagagcgcga acgatgacca cgagagaagt    1380
atattgacca aattgaagca acaatgtggt ggtcagttca cttctaagat ggagggaatg    1440
gttactgatt tgactttggc aagggagaac caaactagtt ttgaggagta tctgagcaat    1500
aatccacaag cgagtcctgg catcgacctg actgttactg ttttaactac tggattttgg    1560
```

-continued

```
ccaagctaca agtcttttga cctcaacctg ccggcagaga tggtaaagtg tgttgaagtt    1620
ttcagagagt tttatcaaac aaaaaccaag catcgaaaac ttacatggat ttactcattg    1680
ggtacttgta acatcagtgg aaaatttgaa ccgaaaacga tggagctgat tgtgacaact    1740
tatcaggctt ctgccctgtt gctattcaat tcttcggata gactaagtta ctcggaaatc    1800
atgacacaat taaatttgag tgacgatgat gtagttagac tactccactc gttgtcatgt    1860
gccaagtata aaattcttaa taaggaacca aatacgaaaa ccatctctcc gaacgatcat    1920
tttgagttca atgcaaaatt ctccgacaaa atgaggagaa taaagatccc tcttccgcct    1980
gtggatgaga aaagaaagt cattgaagat gttgacaagg atcgaaggta tgctattgac     2040
gcctcaatcg tgcgtatcat gaagagtcgg aaagttcttg gtcatcagca actagtgatg    2100
gagtgcgtcg agcaattggg ccgtatgttc aagcccgatt tcaaggcgat aaagaagaga    2160
attgaagacc tgatcactcg ggattatcta gagagagaca aagacaaccc ccacttgttt    2220
aggtacttgg cttga                                                    2235
```

MARKER FOR COMPACT GROWTH IN CUCUMBER

RELATED APPLICATIONS AND INCORPORATION BY REFERENCE

This application is a continuation-in-part application of international patent application Serial No. PCT/EP2016/071179 filed 8 Sep. 2016, which published as PCT Publication No. WO 2017/042272 on 16 Mar. 2017, which claims benefit of NL patent application Serial No. 2015408 filed 8 Sep. 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 9, 2018, is named 43104002350_SL.txt and is 6,428 bytes in size.

FIELD OF THE INVENTION

The present invention relates to a marker for identifying a plant suitable for high-wire cultivation, and to use of the markers.

BACKGROUND OF THE INVENTION

In the high-wire cucumber cultivation, higher planting densities are used to obtain higher yields per m2. In addition, high-wire cultivation allows a longer cultivation period during which the plant produces cucumber fruits. However, not all varieties are fit for this type of cultivation. It is the goal of the present invention to provide a means for identifying such plants.

In WO2009/059777 cucumber plants that are suitable for high-wire cultivation are described. The disclosed cucumber plants express, in comparison with the usual type of long cucumber shorter internodes, shorter lateral shoots, smaller and darker leaves which remain green for longer, less bumpy leaves, smaller flowers, a more horizontal orientation of the leaves, shorter fruits, and above all a slower growth rate. These characteristics are caused by an unknown genetic determinant which is referred to as the "compact gene". It was described that the genetic locus of the compact gene can be demonstrated and monitored with the aid of flanking AFLP markers in descendants obtained by hybridizing a cucumber plant that may comprise this genetic locus with a short cucumber type or a gherkin type plant that does not contain this genetic locus, and the genetic locus in question can be introduced, by hybridization, into every plant that can be hybridized with a cucumber plant according to the present invention.

However, the AFLP markers that are disclosed in the application are not polymorphic in long cucumber types, therefore selecting a long cucumber type that may comprise the compact gene involves first crossing such a plant with a short cucumber or gherkin (both lacking the compact gene) and analyzing the progeny of such cross (e.g. the F1 and/or F2 generation) with one or more of the disclosed AFLP markers linked to the compact locus.

The AFLP markers disclosed in WO2009/059777 are thus not very convenient to work with and the method described therein is very laborious and inefficient. Furthermore, the use of AFLP markers as an identification and monitoring tool has become outdated, because sequencing tools are becoming more sophisticated and less expensive this recent decade. This makes it difficult, if not impossible to find service companies or organizations that can perform AFLP analyses.

Citation or identification of any document in this application is not an admission that such document is available as prior art to the present invention.

SUMMARY OF THE INVENTION

Taking into account the hurdles and issues as described here, there is a need for a convenient and efficient method to monitor the genetic determinant that underlies the compact gene phenotype, a phenotype suitable for high-wire cultivation.

In the research leading to the present invention, it was found that the compact phenotype, or the phenotype suitable for high-wire cultivation, is caused by a mutation in the Cullin1 gene. A plant that has the mutant gene is in particular suitable for high-wire cultivation. Such a plant shows shorter internode length and/or a smaller leaf area and may also display the other characteristics as described herein as the compact growth phenotype. It was found that the mutation in the cucumber Cullin1 gene is a specific substitution at position 147 of SEQ ID NO:1, i.e. downstream of the ATG start codon of the coding sequence (CDS) and may comprise a change from Adenine to Guanine.

FIG. 1 shows the wild type cucumber Cullin1 nucleotide sequence SEQ ID NO:1. FIG. 2 shows the mutant cucumber Cullin1 nucleotide sequence SEQ ID NO:2.

The mutation is a so-called single nucleotide polymorphism (SNP). This SNP is a single nucleotide in the genomic sequence that differs (A/G) between cucumber plants that show the normal phenotype and have an adenine (A) at position 147 of SEQ ID NO: 1 and cucumber plants that may comprise the compact growth phenotype and have a Guanine (G) at position 147 as in SEQ ID NO: 2.

The invention thus relates to a marker for identifying a cucumber plant showing a compact growth phenotype, which may comprise a SNP at position 147 of the sequence of SEQ ID NO:1, wherein the SNP may comprise a change from adenine to guanine.

In one embodiment, the marker may comprise the sequence of SEQ ID NO: 2 or a part thereof, which part may comprise the SNP.

In one embodiment the compact growth phenotype may comprise a shorter internode length and/or smaller leaf area.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 Cucumber Cullin1 coding sequence wild type, SEQ ID NO:1. The nucleotide between brackets indicates the position of the SNP on 147 bp from the start. The wild type form is "A" (adenine), as shown here.

FIG. 2 Cucumber Cullin1 coding sequence mutant "compact", SEQ ID NO:2. The nucleotide between brackets indicates the position of the SNP 147 bp from the start. The wild type form is "A" (adenine), the mutant variant shown here is "G" (guanine).

DETAILED DESCRIPTION OF THE INVENTION

The terms "shorter internode length" and "smaller leaf area" as used herein, are defined as follows.

The term "smaller leaf area" as used herein is the leaf area that displays a reduction in individual leaf area of, in order of increased preference, at least 10%, at least 20%, at least 30%, at least 40%, at least 50%, at least 60%, at least 70%, at least 80% as a result of the homozygous presence of the modified gene of the invention. To investigate the influence of the gene of the invention on the smaller leaf area, a skilled person would have to compare plants having the gene of the invention homozygously with plants that are isogenic to first mentioned plants but do not have the gene of the invention.

The term "shorter internodes" or "shorter internode length" as used herein is internode length that has a reduction in individual length of, in order of increased preference, at least 10%, at least 20%, at least 30%, at least 40%, at least 50%, at least 60%, at least 70%, at least 80% as a result of the homozygous presence of the gene of the invention. To investigate the influence of the gene of the invention on the shorter internode length, a skilled person would have to compare plants having the gene of the invention homozygously with plants that are isogenic to first mentioned plants but without the gene of the invention.

Furthermore the invention relates to the use of the sequence of SEQ ID NO: 2 or a part thereof as a marker for identifying a cucumber plant showing a compact growth phenotype, wherein the part thereof may comprise the SNP.

A marker is a DNA sequence that is polymorphous between individuals and can be used to distinguish one individual from the other. A marker may be a long sequence like a microsatellite or a very short DNA sequence, like a single nucleotide polymorphism (SNP). In the current invention, the variation is a SNP in the Cullin1 gene. Various analytical methods are available detect SNPs in the genome. These include DNA sequencing, capillary electrophoresis, mass spectrometry, single-strand conformation polymorphism (SSCP), single-base extension, electrochemical analysis, denaturing HPLC and gel electrophoresis, restriction fragment length polymorphism, hybridization analysis. The goal of these methods is to determine which allele of the SNP (wild type or mutation) is present in the genome to be tested. The SNP in the genome is the actual marker. When DNA sequencing is used for detection of the SNP the sequence of the gene which may comprise the SNP is determined and afterwards it is assessed which nucleotide is present on position 147. For other analytical methods various derivatives of the actual DNA sequence that may comprise the SNP may be used. These derivatives may comprise for example a DNA molecule that has the complete gene sequence of SEQ ID NO:1 or only a part thereof. In any case, a derivative should comprise the position of the SNP. These derivatives are also comprised in the term "marker".

The term "wild type" as used herein refers in general to the form of an organism, gene, protein, or trait as it would occur in nature, as opposed to a mutated or modified form. In this application wild type refers specifically to the naturally occurring form of the Cullin1 gene, the naturally occurring form of the nucleotide sequence of Cullin1. In particular, "wild type" as used herein refers to the wild type cucumber Cullin1 genomic nucleotide sequence of SEQ ID NO: 1.

The terms "mutant", "mutation", "modification" "modified" and "mutated Cullin1 gene" as used herein are interchangeable and refer to nucleotide changes in the wild type Cullin1 gene that lead to a modified version of the wild type gene. In particular, "mutant" as used herein refers to the mutant cucumber Cullin1 genomic nucleotide sequence of SEQ ID NO: 2.

In general, to identify a cucumber plant with the compact growth phenotype, i.e. showing a shorter internode length and/or a smaller leaf area, it is thus determined in SEQ ID NO:1 whether there is an A or a G on position 147. SEQ ID NO:2 gives the sequence of the mutated version of the Cullin1 gene, which may comprise a G on position 147.

The invention further relates to the use of the SNP of the invention as a marker for identifying cucumber plants showing the compact growth phenotype, i.e. a shorter internode length and/or a smaller leaf area.

In this application the term "A/G" means that the first mentioned nucleotide; adenine (A) is mutated into the nucleotide mentioned last; guanine(G).

The invention further relates to a method for selecting a cucumber plant capable of showing a compact growth phenotype from a population of cucumber plants, which may comprise detecting the presence or absence of a guanine on position 147 of SEQ ID NO:1 in the genome of a plant of a population of cucumber plants, and selecting a cucumber plant which may comprise a guanine on position 147 of SEQ ID NO:1. In a particular embodiment of the method the marker as defined herein is used.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Identification of the Cullin1 Gene Mutation in *Cucumis sativus*

A F2 crossing population made from a commercially available "high wire" cucumber variety, "Hi Lisa", was used to create a new genetic map. In total, 375 markers and 398 F2 lines are used. A QTL analysis performed on these crossing populations revealed a major QTL on chromosome 6 in which one of the alleles is responsible for a compact growth phenotype characterized by a smaller plant length, shorter internode length, and smaller leaf surface. Sequencing of the peak marker of the QTL revealed a SNP present in the marker sequence. The particular sequence was polymorphic in the crossing population. The nucleotide sequence of the major QTL on chromosome 6 was identified by means of BLAST. The best BLAST hits for the sequence all resembled the sequence of the Cullin1 gene. The wild type cucumber nucleotide sequence is shown in FIG. 1.

Example 2

Validation of the Effect of SNP in the Cullin1 Gene on Internode Length and Plant Leaf Area Different populations of *Cucumis sativus* plants, each made with different commercially available 'high wire' varieties, having the compact growth phenotype of shorter internodes, and smaller leaves, were phenotypically and genetically analysed. See Table 1 for the phenotypic and genetic data.

Plants were measured 3 weeks after sowing. For estimating the leaf area, from the second leaf on (not the cotyledons) all leafs present were measured, and the width and the length of a leaf were measured and multiplied with each other to obtain a score for leaf area. In the third column of Table 2, the different haplotypes for the Cullin1 gene SNP are given. The score A means that the SNP marker scored homozygous for the wild type Cullin1 gene, B means homozygous for the modified Cullin1 gene.

In the first population, plants that are homozygous for the modified Cullin1 gene (B), show an internode length that is on average 79% of the length of the plants that are homozygous for the wild type Cullin1 gene (A). The B plants furthermore show a leaf area that is on average 40% of the leaf area of the A plants.

In the second population, the B plants show an internode length that is 65% of the internode length of the A plants and a leaf area that is on average 47% of the leaf area of the A plants.

TABLE 2

Results of phenotypic and genotypic analyses of individual plants of 2 different cucumber lines derived from commercially available high wire varieties (Nun 02944, Hi-Tona). The internode length is defined as the length of the main stem divided by the number of internodes. The leaf area is estimated by measuring the length and the width from all leafs present on a plant, starting with the second leaf (not the cotyledons), multiplying the leaf length and width, and computing the average per plant. For the scores of the Cullin1 SNP, score A means that the marker scored A homozygous (wildtype), B means homozygous (modified)

| Plant material | Cullin1 haplotype | Internode length (H/I) | Leaf area (J × K) |
|---|---|---|---|
| Nun 02944 pl1 | B | 4.3 | 208 |
| Nun 02944 pl15 | B | 5.7 | 285 |
| Nun 02944 pl7 | B | 5.8 | 238 |
| Nun 02944 pl9 | B | 6.1 | 216 |
| Nun 02944 pl8 | B | 6.4 | 285 |
| Nun 02944 pl17 | B | 6.6 | 238 |
| Nun 02944 pl6 | A | 6.7 | 550 |
| Nun 02944 pl3 | A | 6.8 | 616 |
| Nun 02944 pl10 | A | 6.8 | 567 |
| Nun 02944 pl13 | A | 7.2 | 675 |
| Nun 02944 pl5 | A | 8 | 690 |
| Nun 02944 pl8 | A | 8.6 | 546 |
| Hi-Tona pl4 | B | 3.9 | 156 |
| Hi-Tona pl8 | B | 4.1 | 195 |
| Hi-Tona pl6 | B | 4.3 | 238 |
| Hi-Tona pl2 | B | 4.4 | 195 |
| Hi-Tona pl11 | B | 4.8 | 208 |
| Hi-Tona pl5 | B | 4.9 | 224 |
| Hi-Tona pl9 | A | 5.1 | 336 |
| Hi-Tona pl10 | A | 7 | 480 |
| Hi-Tona pl14 | A | 7.3 | 437 |
| Hi-Tona pl12 | A | 7.4 | 483 |

The invention is further described by the following numbered paragraphs:

1. Marker for identifying a cucumber plant showing a compact growth phenotype, comprising a SNP on position 147 of the sequence of SEQ ID NO:1, wherein the SNP comprises a change from adenine to guanine.

2. Marker of paragraph 1, comprising the sequence of SEQ ID NO:1 or SEQ ID NO:2 or a part thereof, which part comprises the SNP as defined in paragraph 1.

3. Marker of paragraph 1 or 2, wherein the compact growth phenotype comprises the cucumber plant having a shorter internode length and/or a smaller leaf area.

4, Marker of any one of the paragraphs 1-3, wherein a shorter internode length comprises a reduction of at least 10% as a result of the homozygous presence of the modified gene of the invention.

5, Marker of any one of the paragraphs 1-4, wherein a smaller leaf area comprises a reduction in area of at least 10% as a result of the homozygous presence of the modified gene of the invention.

6. Use of a marker of any of the paragraphs 1-5 for identifying a cucumber plant showing a shorter internode length and/or a smaller leaf area.

7. Method for selecting a cucumber plant capable of showing a compact growth phenotype from a population of cucumber plants, comprising detecting the presence or absence of a guanine on position 147 of SEQ ID NO:1 in the genome of a plant of a population of cucumber plants, and selecting a cucumber plant comprising a guanine on position 147 of SEQ ID NO:1.

8. Method for selecting of paragraph 7, wherein the marker as defined in any of the paragraphs 1-5 is used for detecting.

Having thus described in detail preferred embodiments of the present invention, it is to be understood that the inven- tion defined by the above paragraphs is not to be limited to particular details set forth in the above description as many apparent variations thereof are possible without departing from the spirit or scope of the present invention.

What is claimed is:

1. A method for identifying a cucumber plant capable of showing a shorter internode length and/or a smaller leaf area comprising isolating a nucleotide sample for genomic DNA analysis from the plant and analyzing the nucleotide sample for the presence or absence of a guanine on position 147 of SEQ ID NO:1 in the DNA, and identifying a cucumber plant as a cucumber plant capable of showing a shorter internode length and/or a smaller leaf area if its genome comprises a guanine on position 147 of SEQ ID NO:1.

2. The method of claim 1, wherein the analyzing comprises detecting a marker comprising a SNP at position 147 of SEQ ID NO: 1 changing from adenine to guanine.

3. The method of claim 2, wherein the marker comprises the sequence of SEQ ID NO:1 or SEQ ID NO:2, or a part thereof, wherein the part comprises the SNP as defined in claim 2.

4. The method of claim 1, wherein the nucleic acid sample is a DNA sample.

5. The method of claim 4, wherein the analyzing comprises detecting a marker comprising a SNP at position 147 of SEQ ID NO: 1 changing from adenine to guanine.

6. The method of claim 5, wherein the marker comprises the sequence of SEQ ID NO:1 or SEQ ID NO:2, or a part thereof, wherein the part comprises the SNP as defined in claim 2.

* * * * *